(12) United States Patent
Klee et al.

(10) Patent No.: US 7,503,340 B2
(45) Date of Patent: Mar. 17, 2009

(54) SYSTEM AND METHOD FOR CONTROLLING FLUID FLOW

(75) Inventors: Matthew S. Klee, Wilmington, DE (US); Michael Q. Thompson, Coatesville, PA (US); James D. McCurry, Quakertown, PA (US); Paul C. Dryden, West Grove, PA (US)

(73) Assignee: Agilent Technologies, Inc., Santa Clara, CA (US)

( * ) Notice: Subject to any disclaimer, the term of this patent is extended or adjusted under 35 U.S.C. 154(b) by 396 days.

(21) Appl. No.: 11/240,421

(22) Filed: Sep. 30, 2005

(65) Prior Publication Data

US 2007/0074766 A1   Apr. 5, 2007

(51) Int. Cl.
*F16K 31/12* (2006.01)
*G01N 30/02* (2006.01)

(52) U.S. Cl. .................................. 137/487.5; 73/23.36
(58) Field of Classification Search ............. 137/487.5; 96/104; 422/89; 95/86; 251/129; 436/55
See application file for complete search history.

(56) References Cited

U.S. PATENT DOCUMENTS

| | | | | |
|---|---|---|---|---|
| 3,901,081 A | * | 8/1975 | Adiutori | 374/29 |
| 5,281,256 A | * | 1/1994 | Sacks et al. | 95/86 |
| 5,545,252 A | * | 8/1996 | Hinshaw et al. | 95/15 |
| 5,868,159 A | * | 2/1999 | Loan et al. | 137/334 |
| 6,494,078 B1 | | 12/2002 | Klee | |
| 6,706,535 B2 | * | 3/2004 | Sacks et al. | 436/161 |
| 6,956,123 B2 | * | 10/2005 | Johnson et al. | 549/510 |

FOREIGN PATENT DOCUMENTS

GB   2303885 A   5/1997

* cited by examiner

*Primary Examiner*—John Rivell
*Assistant Examiner*—Atif H Chaudry (57) ABSTRACT

A system for controlling fluid flow comprises a first fluid conduit having a length, an inner diameter, an input pressure and an output pressure, and a second fluid conduit having a length, an inner diameter, an input pressure and an output pressure where the output pressure of the first fluid conduit is the input pressure of the second fluid conduit. The system also comprises a pressure sensor configured to determine the output pressure of the first fluid conduit, and a controller configured to control the output pressure of the first fluid conduit, thereby establishing a desired fluid flow through the second fluid conduit based on the length of the second fluid conduit, the inner diameter of the second fluid conduit, the temperature of the second fluid conduit and the type of fluid flowing in the second fluid conduit.

18 Claims, 5 Drawing Sheets

```
                    START
                      ↓
    ┌─────────────────────────────────────────┐
    │ SPECIFY/DETERMINE COLUMN LENGTH, INNER  │
    │ DIAMETER AND OTHER PHYSICAL PARAMETERS  │
502 │         FOR COLUMN 1 AND COLUMN 2       │
    └─────────────────────────────────────────┘
                      ↓
         ┌────────────────────────┐
     504 │  SPECIFY CARRIER GAS   │
         └────────────────────────┘
                      ↓
         ┌────────────────────────┐
         │  SPECIFY DESIRED FLOW  │
     506 │      FOR COLUMN 1      │
         └────────────────────────┘
                      ↓
       ┌──────────────────────────────┐
   508 │ SPECIFY DESIRED FLOW FOR COLUMN 2 │
       └──────────────────────────────┘
                      ↓
    ┌──────────────────────────────────────────┐
    │ SPECIFY/DETERMINE P3 (E.G., ATMOSPHERIC  │
512 │   PRESSURE) AND OVEN TEMPERATURE         │
    └──────────────────────────────────────────┘
                      ↓
  ┌──────────────────────────────────────────────┐
514 │ SET AUXILIARY EPC PRESSURE (P2) BASED ON KNOWN │
  │  PARAMETERS TO ACHIEVE DESIRED FLOW IN COLUMN 2 │
  └──────────────────────────────────────────────┘
                      ↓
  ┌──────────────────────────────────────────────┐
516 │   SET INLET PRESSURE (P1) BASED ON KNOWN    │
  │  PARAMETERS TO ACHIEVE DESIRED FLOW IN COLUMN 1 │
  └──────────────────────────────────────────────┘
                      ↓
  ┌──────────────────────────────────────────────┐
  │ MONITOR AND CONTROL INLET PRESSURE (P1)      │
518 │    AND AUXILIARY EPC PRESSURE (P2)          │
  └──────────────────────────────────────────────┘
                      ↓
  ┌──────────────────────────────────────────────────┐
  │ ADJUST INLET PRESSURE (P1) AND AUXILIARY EPC      │
  │ PRESSURE (P2) BASED ON CHANGES IN TEMPERATURE     │
  │ AND/OR P3 TO MAINTAIN DESIRED FLOW THROUGH        │
  │ COLUMN 1 AND COLUMN 2                             │
520 └──────────────────────────────────────────────────┘
                      ↓
                    END
```

FIG. 5

SYSTEM AND METHOD FOR CONTROLLING FLUID FLOW

BACKGROUND

Many analysis applications, such as chromatography and spectrometry, rely on the flow of fluid through one or more tubes and couplings. For example, in gas chromatography, one or more tubes, referred to as columns, are used to analyze a sample of material to determine its contents. In some applications, a first column is coupled to a second column, and, in other applications, a single column may be coupled to one or more restrictor devices, which may be coupled to various types of detectors. Regardless of the system topology, it is desirable to control the flow through the column or columns so that accurate analysis can be performed. The control of fluid flow is particularly important when performing multi-dimensional analysis, in which two or more columns (in the case of multi-dimensional chromatography) or two or more detectors (in the case of multi-dimensional detection) are used to perform the analysis.

The precise measurement and control of low flow rates, on the order of one milliliter per minute (mL/min), is difficult, costly and generally problematic. The measurement of pressure is often easier, less costly and more accurate, especially in systems with multiple flow paths and/or discontinuous physical dimensions or environment. Flow rates can be accurately deduced for open tubular flow paths using known relationships among pressures, physical dimension of the open tubes, temperature, and physical parameters of the type of gas flowing through the tubes.

During analysis, one or more variables, such as the temperature of the column in the case of chromatography, are frequently changed to perform the analysis. Further, in chromatography it is often necessary to change a column after some number of uses or to remove a contaminated portion of the column and reconnect it to the analysis device. Changing the temperature during analysis or altering the dimensions of the column alters the flow characteristics through the column, and necessitates the recomputation of various parameters so that the flow through the column may be accurately inferred and then controlled by adjusting pressure(s) to obtain the desired result. The inability to control the flow characteristics with multiple coupled tubes in an automated fashion in the current state of the art limits the utility and acceptance of multidimensional analysis techniques.

Therefore, it would be desirable to have the ability to automatically alter the flow in a chromatographic column, or a plurality of other open tubes, during analysis and to compensate for physical changes to the analysis systems.

SUMMARY OF THE INVENTION

According to an embodiment, a system for controlling fluid flow comprises a first fluid conduit having a length, an inner diameter, an input pressure and an output pressure, and a second fluid conduit having a length, an inner diameter, an input pressure and an output pressure where the output pressure of the first fluid conduit is the input pressure of the second fluid conduit. The system also comprises a pressure sensor configured to determine the output pressure of the second fluid conduit, and a controller configured to control the outlet pressure of the first fluid conduit, thereby establishing a desired fluid flow through the second fluid conduit based on the length of the second fluid conduit, the inner diameter of the second fluid conduit, the temperature of the second fluid conduit and the type of fluid flowing therein.

Other embodiments of the invention will be discussed with reference to the figures and to the detailed description of the preferred embodiments.

BRIEF DESCRIPTION OF THE FIGURES

The invention will be described by way of example, in the description of exemplary embodiments, with particular reference to the accompanying figures.

DETAILED DESCRIPTION

While described below as used in a gas chromatograph, the system and method for controlling fluid flow can be used in any analysis application where it is desirable to automatically control the flow of a fluid through two or more fluid conduits, or tubes, in which the fluid pressure at the beginning, the end and at each junction of the coupled fluid conduits is known or can be determined. As used herein, the term flow is intended to include forms of mass flow, programmed mass flow, or volumetric flow and/or forms of linear velocity such as programmed linear velocity, average linear velocity, inlet, outlet, or instantaneous linear velocity through a fluid conduit.

Figure 1:
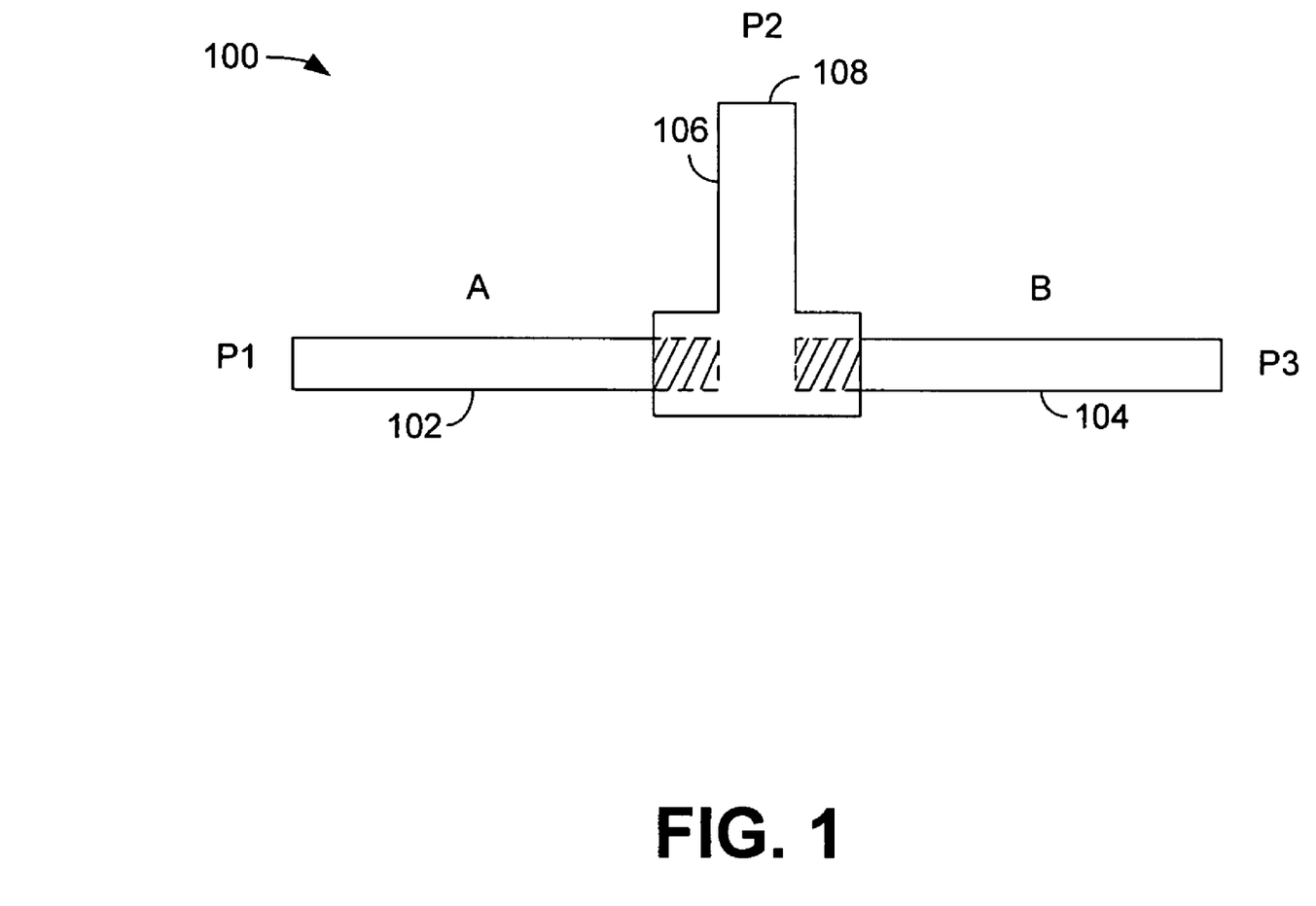
FIG. 1 is a schematic diagram conceptually illustrating the principle of fluid flow automation in accordance with an embodiment of the invention.

FIG. 1 is a schematic diagram conceptually illustrating the principle of fluid flow automation in accordance with an embodiment of the invention. The fluid system 100 includes a first fluid conduit 102 and a second fluid conduit 104 coupled together through a fluid coupling 106. Although illustrated conceptually, the fluid conduits 102 and 104 can represent two chromatographic columns coupled together for use in multi-dimensional chromatography. However, it should be understood that multi-dimensional chromatography is merely one example of a use of the fluid flow automation of the invention. In another embodiment the fluid coupling 102 may represent a chromatographic column and the fluid conduit 104 may represent a restrictor, which may have another analysis device, such as a mass spectrometer coupled thereto. In alternative embodiments, the fluid conduits 102 and 104 can be any tubes. Further, the principles of the invention are also applicable to systems having more than two tubes coupled in series.

The fluid couplings 102 and 104 are illustrated as being simply threaded into the fluid coupling 106. However, other attachment means are possible. A fluid pressure is illustrated as P1 and represents an input fluid flow into fluid conduit 102. The output pressure of fluid conduit 102, which is also the input pressure to fluid conduit 104 is illustrated as fluid pressure P2. The fluid pressure P2 can be measured via the port 108 of fluid coupling 106. The fluid pressure illustrated as P3 represents the output pressure of fluid conduit 104.

For purposes of this description, it is assumed that the dimensions, typically the length and inner diameter, of the fluid conduits 102 and 104 are different. This is analogous to a coupled-column chromatograph in which some or all of the flow from a first column (fluid conduit 102) passes to a second column (fluid conduit 104). Furthermore, in the fluid system 100, the temperature of the fluid conduits 102 and 104 is known, or can be accurately measured, and the properties of the fluid flowing through the fluid conduits 102 and 104 is known. Using again the example of chromatography, the fluid conduits 102 and 104 are typically located in a thermal chamber so that the temperature can be raised and lowered, and the gas flowing through the columns is selected based on accepted practices of chromatography. The flow through the fluid conduits 102 and 104 may be different, independent of each other. Even if the columns are identical the flows may be different for one or more reasons. As will be described below, it is possible to control the flow through two or more columns at known, and possibly different temperatures, given the column dimensions, and carrier gas type.

The ability to measure, detect, and/or otherwise know the pressures P1, P2 and P3 in the fluid conduits 102 and 104, the dimensions of the fluid conduits 102 and 104, the characteristics of the fluid traveling through the fluid conduits 102 and 104 and the temperature of conduits 102 and 104 allows all of the flow parameters through fluid conduits 102 and 104 to be calculated. Essentially, by knowing the above-identified parameters and the pressure P2, it is possible to control the flow of fluid through the fluid conduits 102 and 104 by measuring and adjusting P1, P2 and P3.

The mass flow through fluid conduit 102 equals the mass flow through the fluid conduit 104 if fluid conduits 102 and 104 are pneumatically, or hermetically sealed to the fluid coupling 106. However, the system and method for controlling fluid flow is applicable even if the flow through each conduit is different, so long as the pressure P2 is known. If the flow through the fluid conduit 102 is greater than the flow through the fluid conduit 104, excess flow from the fluid conduit 102 can be bled off (e.g., removed through the fluid coupling 106), or if flow from the fluid conduit 102 is less than that desired for the fluid conduit 104, additional flow can be added (e.g., added through the fluid coupling 106) such that the desired pressure P2 is maintained.

The term constant flow, as used herein defines a subset of possible flow control that can be accomplished. In one embodiment, the term "constant flow" defines a mode of flow control wherein constant mass flow is maintained throughout a chromatographic run even as oven temperature is changing. This constant mass flow is also directly related to constant instantaneous velocity (linear velocity as measured at a specific point on along a column). In other embodiments, the term "constant flow" may mean constant average linear velocity, which is different than constant mass flow.

As will be described below, the system and method for controlling fluid flow generates a desired flow in coupled columns. The desired flow includes, as non-limiting examples, constant mass flow, constant volumetric flow, constant average linear velocity, programmed flow, and other flows. In addition, the system and method for automating fluid flow allows for the independent control of desired flow in each of a number of coupled tubes.

Figure 2:
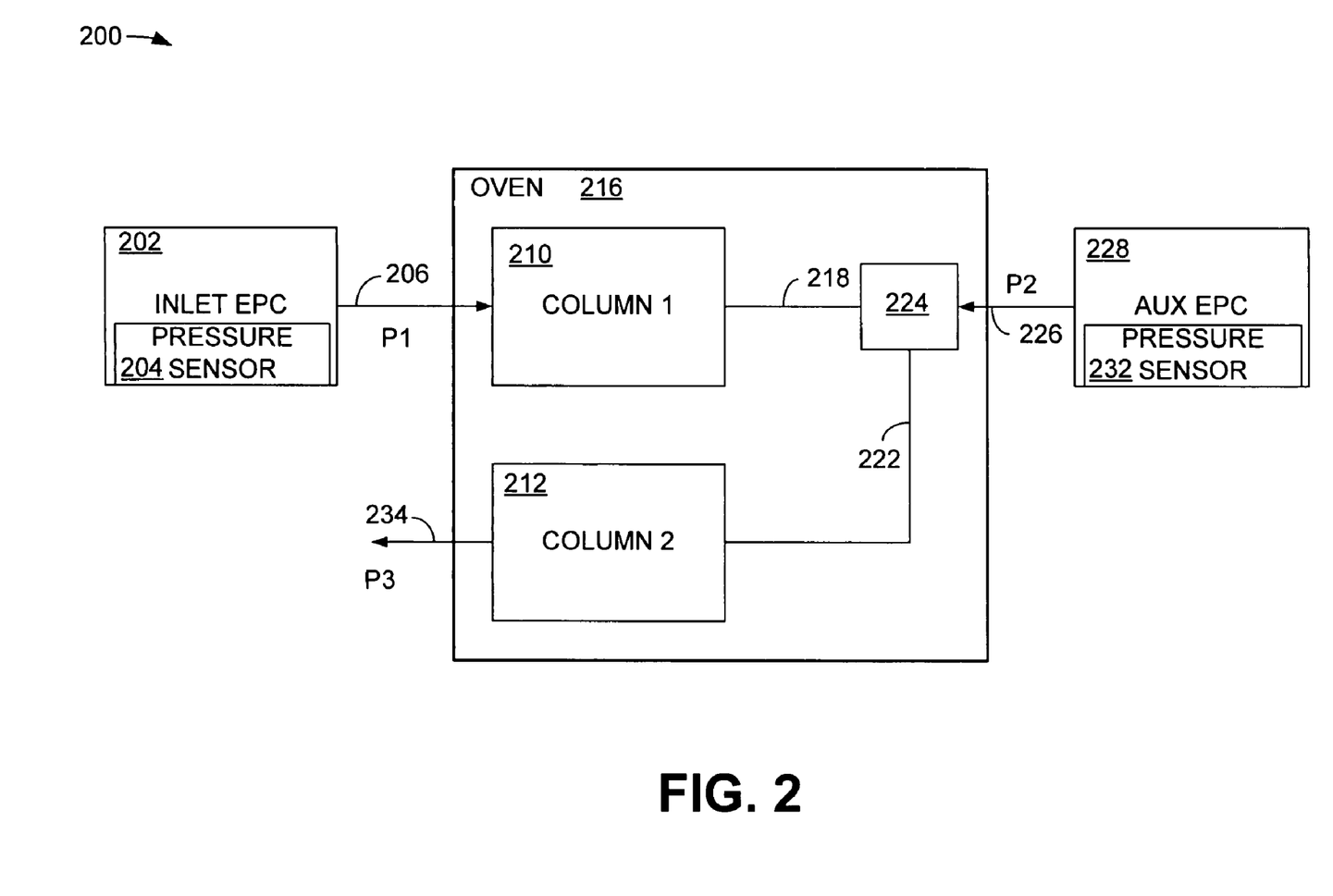
FIG. 2 is a schematic representation of the conceptual diagram of FIG. 1 substituting elements of a chromatograph for the elements described in FIG. 1.

FIG. 2 is a schematic representation of the conceptual diagram of FIG. 1 substituting elements of a chromatograph for the elements described in FIG. 1. The elements shown in FIG. 2 do not constitute a complete chromatograph. Rather, the elements in FIG. 2 illustrate the concepts of the system and method for controlling fluid flow described above in FIG. 1 as applied to the basic elements of a multi-dimensional chromatograph. Further, while described in FIG. 2 as applied to a chromatograph, the system and method for controlling fluid flow in accordance with embodiments of the invention can be applied to other fluid control applications in which it is desirable to control the pressure and flow of fluid through two or more fluid conduits.

Generally, many instrumental methods of chemical analysis use one or more sample tubes to collect, concentrate, and transfer sample material to, through, and/or out of the analysis device. The sample tube, sometimes referred to as a capillary tube, or a capillary column, is connected to an analysis device, such as, for example, a gas chromatograph, a mass spectrometer, a detector, and/or to another tube, using a fluid-tight seal. The material that flows through the tube generally includes the mobile phase. In gas chromatography, the mobile phase is also referred to as the "carrier gas." During sample analysis, sample material to be analyzed and carrier gas flow through the tube. Sometimes the tubing through which there is flow has an immobilized or stationary coating on its surface and sometimes the tubing is filled with a packing material. The coating and packing are referred to as a "stationary phase" when their purpose is to effect sample separation. The tube containing the stationary phase is called the "separation column" or simply "the column."

In chromatography, a sample is introduced into the "flow path" which is a continuous series of sealed connecting tubes, fittings, and at least one column. The sample is carried through the flow path by the mobile phase. A sample of material generally comprises a mixture containing a multiplicity of compounds. The purpose of chromatography is to separate components in the mixture such that their identity and/or quantity can be determined. Separation occurs by the differential retardation of sample components as they travel through the column through interaction with the stationary phase. Each sample component will have a characteristic delay between the time it was introduced into the chromatographic system and the time that it is detected after it elutes from the separation column. This characteristic time is called its "retention time." Some minimum amount of difference in retention time differentiates sample components chromatographically.

In some chromatographic analysis applications, it is desirable to use at least two columns and transfer the elutant from a first column to a second column for improved results. This type of chromatography is generally referred to as multi-dimensional chromatography. In multi-dimensional chromatography, it is desirable to have the ability to individually control the flow of the material through the two, or more, columns.

Referring now to FIG. 2, an embodiment of the system and method for controlling fluid flow is illustrated using chromatograph portion 200. The chromatograph portion 200 comprises an inlet electronic pneumatic control (EPC) element 202. The inlet EPC element 202 further includes an electronic pressure sensor 204. The inlet EPC element 202 provides the pressure P1 over fluid line 206 to the first column 210. The first column 210 in FIG. 2 is analogous to the first fluid conduit 102 of FIG. 1. The output of the first column 210 is supplied via fluid connection 218 to a junction 224. The junction 224 can be what is referred to as a pressure monitored junction, a purged junction, a purged union, or any other multiple port fluid coupling known to those skilled in the art.

The junction 224 is coupled to a second column 212 via fluid connection 222 and to an auxiliary EPC element 228, also referred to as a junction pressure control element. The second column 212 is analogous to the second fluid conduit 104 of FIG. 1, and the junction 224 is analogous to the fluid coupling 106 of FIG. 1. The auxiliary EPC element 228 includes an electronic pressure sensor 232. The output of the second column is provided via fluid connection 234. Typically, the output of the second column 212 could be coupled to a detector at pressure P3 which could be at atmospheric pressure, vacuum, or other known, assumed or measured pressure.

The first column 210 and the second column 212 are located within an oven 216. The oven 216 is controlled during chromatographic analysis to raise and lower the temperature of the first column 210 and the second column 212, either together or individually depending on the analysis being performed. The individual temperature control of the first column 210 and the second column 212 implies that the oven 216 include at least two independently controlled temperature zones.

The inlet EPC element 202 provides the input pressure P1 to the first column 210. The output of the first column 210 at the junction 224, which is also the input of the second column 212, is the pressure P2 described above. In this embodiment of the system and method for automating fluid flow, the auxiliary EPC element 228 uses a combination of the electronic pressure sensor 232 and pressure control to maintain the desired pressure at the output of the first column 210 (and therefore, the input pressure at the second column 212). The pressure P3 is the known, assumed, or measured pressure at the output of the second column 212.

The ability to measure, detect, and/or otherwise know the pressures P1, P2 and P3 in the first column 210 and the second column 212, the temperatures of the first column 210 and the second column 212, the dimensions of the first column 210 and the second column 212 and the characteristics of the fluid traveling through the first column 210 and the second column 212 allows all of the flow parameters through first column 210 and the second column 212 to be calculated. Essentially, by knowing the above-identified parameters, the pressures P1, P2 and P3, it is possible to control the flow of fluid through the first column 210 and the second column 212 by adjusting one or more of the pressures P1, P2, and P3.

As an example, assume that the first column 210 has different dimensions than the second column 212. Assume also that the desired flow through the first column 210 is 0.9 milliliters per minute (mL/min), and the desired flow through the second column 212 is 1.0 mL/min. Assume also that the pressure P3 is known and the pressures P1 and P2 are set such that the target flows are achieved through each column. As the temperature of the oven 216 changes, the flow through the first column 210 and the second column 212 will change due to the change in the viscosity of the carrier gas flowing through the first column 210 and the second column 212 as a result of the temperature change. Depending on whether the temperature increases or decreases, the flow will either increase or decrease. In many analysis applications, it is desirable to maintain a constant flow through the first column 210 and second column 212 throughout the analysis, which may include multiple temperature excursions.

Since P3 is often fixed, static, or not actively controlled, an embodiment of the invention is to first establish conditions in the second (or the last tube in a sequence of more than two tubes) column and work back to establishing conditions in the first column to achieve the desired flow. In this example, it is possible to control the flow through the second column 212 by adjusting the pressure P2, using the auxiliary EPC element 228, based on the oven temperature, the pressure P3, and the desired flow through the second column 212 (1.0 mL/min.). It is then possible to calculate a pressure P1 based on the desired flow through the first column 210 (0.9 mL/min.), the temperature of the oven 216, and the pressure P2 at the outlet of the first column 210 using the electronic pressure sensor 232. The availability of the auxiliary EPC element 228 allows the independent adjustment and control of the pressure P2, and therefore, control of the flow through the second column 212. The combination of the inlet EPC element 202 and the known pressure P2 allows the adjustment of the pressure P1, which provides flow control through the first column 210 independent of the second column 212.

In one example, during analysis an early eluting compound goes through the junction 224 and onto the second column 212. At a later time the inlet pressure P1 is decreased below the pressure P2 creating a backflush flow in the first column 210. The flow through the second column 212 remains constant as long as the pressure P2 and temperature remain constant.

In another example, the pressure P3 is equivalent to atmospheric pressure. As atmospheric pressure changes, the pressure P2 is adjusted in response to maintain desired flow in the second column 212. Controlling the pressure P2 for constant flow with atmospheric pressure compensation is chromatographically desirable.

Figure 3:
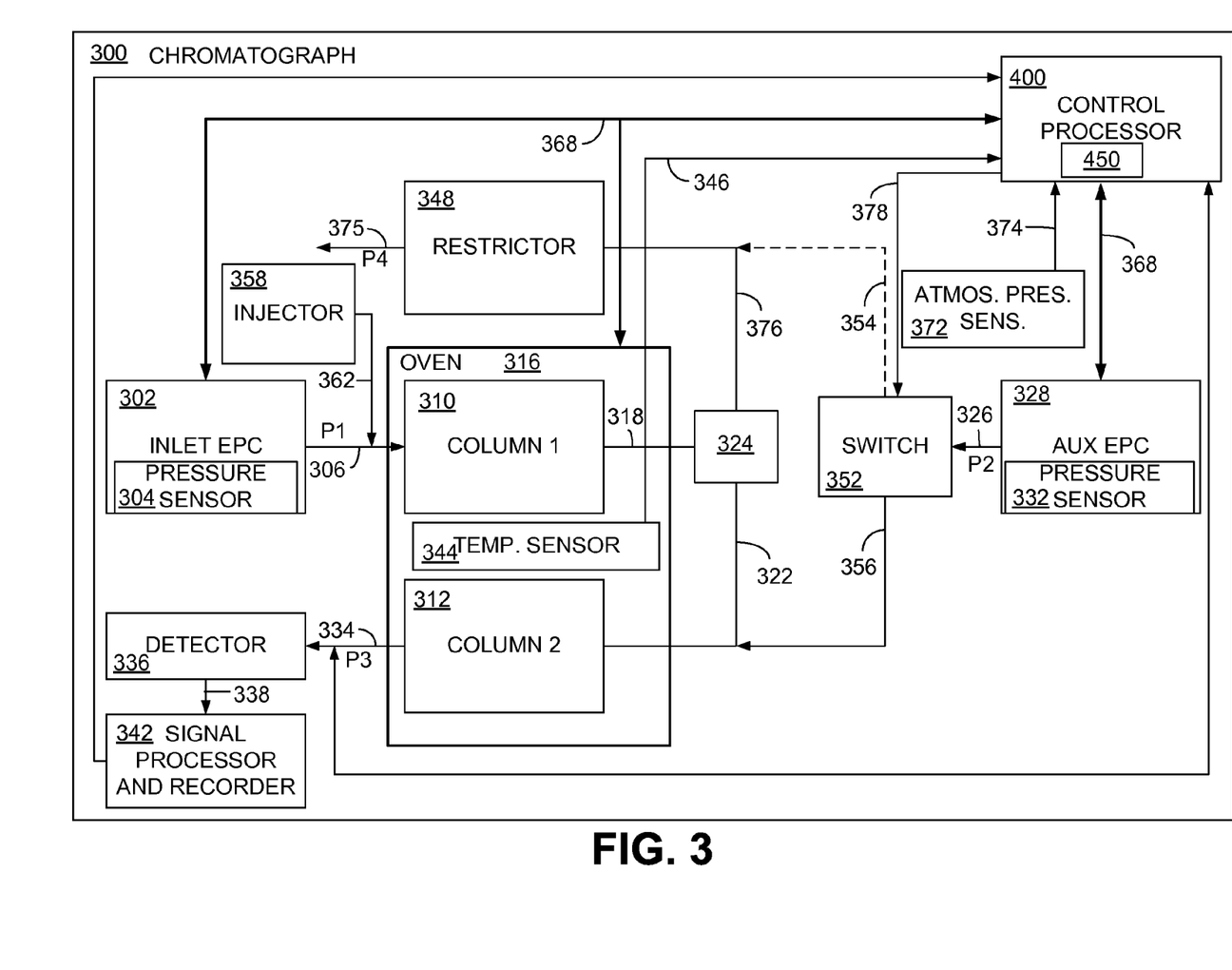
FIG. 3 is a block diagram illustrating a chromatograph in accordance with an embodiment of the system and method for automating fluid flow.

FIG. 3 is a block diagram illustrating a chromatograph 300 in accordance with an embodiment of the system and method for controlling fluid flow. As stated above, chromatography is one example of a system in which the system and method for controlling fluid flow can be implemented. The chromatograph 300 includes some elements that are similar to the elements described in FIG. 2. The elements in FIG. 3 that are similar to the above-described elements are denoted by the numbering convention 3XX, where XX corresponds to a similar element in FIG. 2. For example, the inlet EPC element 302 in FIG. 3 is similar to the inlet EPC element 202 of FIG. 2.

The chromatograph 300 comprises an inlet EPC element 302, which includes an electronic pressure sensor 304. The inlet EPC element 302 provides the pressure P1 over fluid line 306 to the first column 310. An injector 358 provides a sample of material that is to be analyzed via fluid connection 362 to the inlet (not shown) of the first column 310. The output of the first column 310 is supplied via fluid connection 318 to a junction 324. The junction 324 can be what is referred to as a pressure monitored junction, purged junction, a purged union, or any other multiple port fluid coupling known to those skilled in the art.

The junction 324 is coupled to a second column 312 via fluid connection 322 and to a restrictor 348 via fluid connection 376. In some applications, it is desirable for the restrictor to have a variable geometry. However, a variable restrictor adds complexity because it must be precisely monitored and controlled. In some applications, an additional column may be implemented instead of the restrictor 348. Regardless of the manner of implementation, the flow from the first column 310 travels either through fluid connection 322 or fluid connection 376. The pressure, P2, (the junction pressure) is preferably accurately monitored and compensated in an application-appropriate time frame. In accordance with an embodiment of the invention, the system and method for controlling fluid flow allows the use of a fixed restrictor, which is simple to implement. The disposition of the output of the restrictor on connection 376 may vary depending on the needs of the implementation. However, because it is a part of the flow system, the output pressure, whether P3 or another pressure, such as the pressure P4 on connection 375, should be known, assumed or measured.

The output of the second column 312 is coupled via fluid connection 334 to a detector 336. The detector 336 is intended to represent any of a number of different detection devices that may be coupled to the second column 312. For example, the detector 336 can be a mass spectrometer (vacuum), or other detection device at any known, assumed, or measured pressure P3. The output of the detector 336 is processed by a signal processing and recording element 342, and used in any fashion known to those skilled in the art.

A switch 352 is located between the junction 324 and the auxiliary EPC element 328. The switch 352 can be, for example, an electromechanical solenoid switch that is controlled from a control processor 400 via connection 378. The switch 352 directs flow from auxiliary EPC element 328 such that the output of the first column 310 can be directed to either the second column 312 or to the restrictor 348. The auxiliary EPC element 328 includes an electronic pressure sensor 332. The output of the auxiliary EPC element 328 is coupled via fluid connection 326 to the switch 352. The output of the auxiliary EPC element 328 is the pressure P2 described above, also referred to as the junction pressure.

The first column 310 and the second column 312 are located within an oven 316. The oven 316 is coupled to the control processor via communication bus 368 and is controlled during chromatographic analysis to raise and lower the temperature of the first column 310 and the second column 312, independently, if desired, depending on the analysis being performed. The oven 316 includes a temperature sensor 344, which is coupled to the control processor 400 via connection 346, or via communication bus 368.

The chromatograph 300 also includes an atmospheric pressure sensor 372 coupled to the control processor 400 via connection 374. The atmospheric pressure sensor 372 senses the atmospheric pressure in the chromatograph 300 and reports the pressure to the control processor 400. For the cases where the pressure P3 (on connection 334) and/or the pressure P4 (on connection 375) are at atmospheric pressure, the pressure sensor 372 measures P3 and/or P4. Although illustrated in FIG. 3 as a separate element, the atmospheric pressure sensor 372 may be integrated into the control processor 400.

The control processor is coupled to the inlet EPC element 302, the oven 316 and the auxiliary EPC element 328 via communication bus 368 to control the functions and operation of the chromatograph 300. The control processor 400 executes flow automation software 450, which will be described in greater detail below.

The inlet EPC element 302 provides the input pressure P1 to the first column 310. The output of the first column 310 at the junction 324, which is also the input of the second column 312 and the restrictor 348, is the pressure P2 described above and the outlet of the second column 312 is at atmospheric pressure as measured by the atmospheric pressure sensor 372. In this embodiment of the system and method for automating fluid flow, the auxiliary EPC element 328 sets the pressure P2 thereby establishing the input pressure at the second column 312 and the restrictor 348 and therefore, the pressure at the output of the first column 310. The pressure P3 is the pressure at the output of the second column 312 (as measured by atmospheric pressure sensor 372).

The ability to measure, detect, and/or otherwise know the inlet and outlet pressures of each column 310 and 312, the dimensions of the first column 310 and the second column 312 (and the restrictor 348), the atmospheric and oven temperatures, and the characteristics of the fluid traveling through the first column 310 and the second column 312 (and the restrictor 348) allows all of the flow parameters through first column 310 and the second column 312 (or the restrictor 348) to be calculated. Essentially, by knowing the above-identified parameters and the pressure P2, P3 (and P4 if different than P3) it is possible to independently control the flow of fluid through the first column 310 and the second column 312 (and the restrictor 348) by adjusting P1 and P2. The pressures P1 and P2 are adjusted in real-time, or in near-real-time, by the control processor 400 executing the flow automation software 450.

Figure 4:
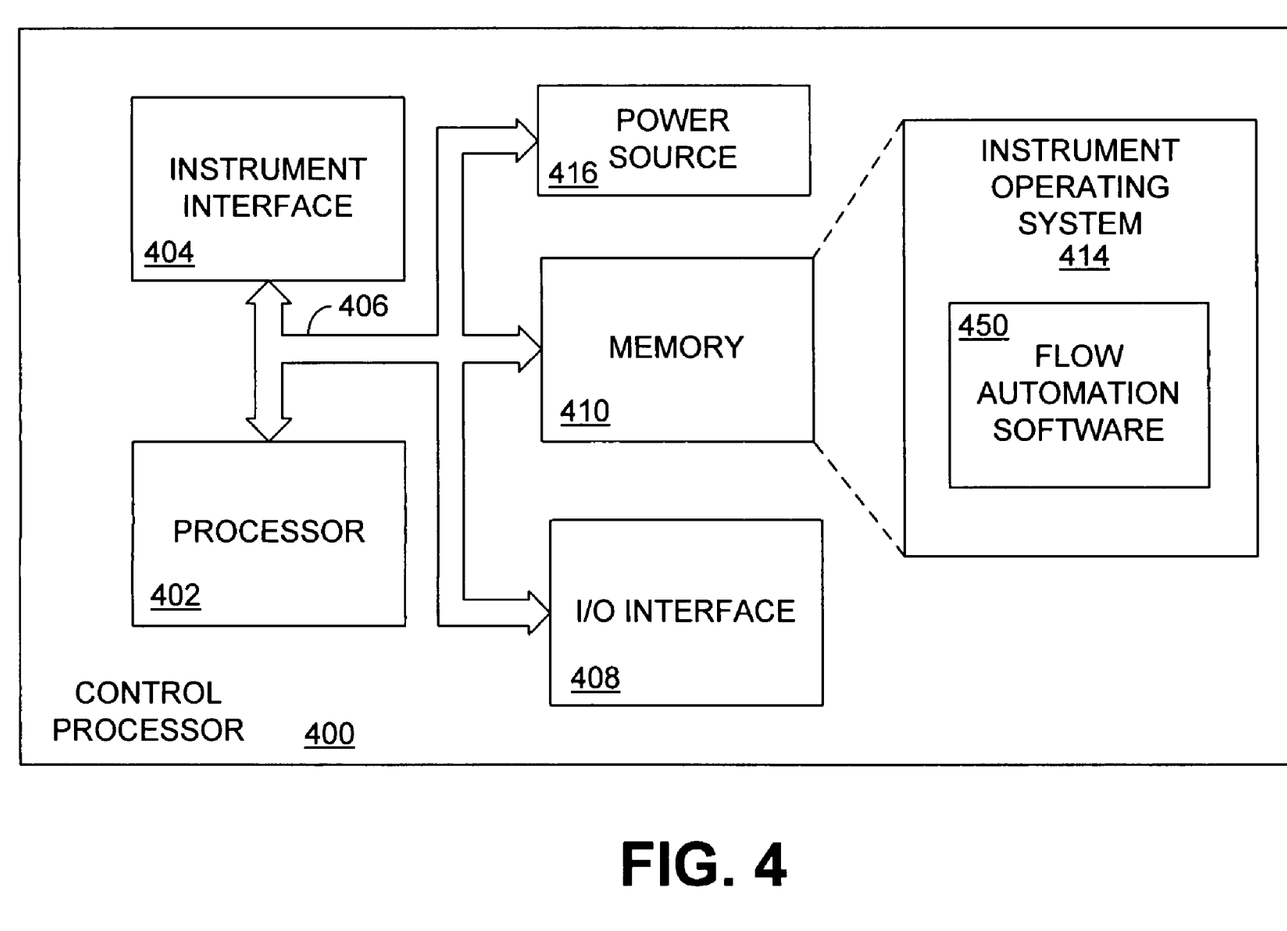
FIG. 4 is a block diagram illustrating an embodiment of the control processor of FIG. 3.

FIG. 4 is a block diagram illustrating an embodiment of the control processor 400 of FIG. 3. The control processor 400 can be any computer based control processor for controlling the operations of the chromatograph 300 of FIG. 3. Further, the control processor 400 may be internal or external to the chromatograph 300. The system and method for controlling fluid flow can be implemented in hardware, software, or a combination of hardware and software. When implemented in hardware, the system and method for controlling fluid flow can be implemented using specialized hardware elements and logic. When the system and method for controlling fluid flow is implemented partially in software, the software portion can be used to control various operating aspects of an analysis device to control the flow of fluid through the analysis device. The software can be stored in a memory and executed by a suitable instruction execution system (microprocessor). The hardware implementation of the system and method for controlling fluid flow can include any or a combination of the following technologies, which are all well known in the art: discrete electronic components, a discrete logic circuit(s) having logic gates for implementing logic functions upon data signals, an application specific integrated circuit having appropriate logic gates, a programmable gate array(s) (PGA), a field programmable gate array (FPGA), etc.

The software for the system and method for controlling fluid flow comprises an ordered listing of executable instructions for implementing logical functions, and can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM), a read-only memory (ROM), an erasable programmable read-only memory (EPROM or Flash memory) (magnetic), an optical fiber (optical), and a portable compact disc read-only memory (CDROM) (optical). Note that the computer-readable medium could even be paper or another suitable medium upon which the program is printed, as the program can be electronically captured, via for instance, optical scanning of the paper or other medium, then compiled, interpreted or otherwise processed in a suitable manner if necessary, and then stored in a computer memory.

The control processor 400 comprises a processor 402, memory 410, input/output (I/O) interface 408, power source 416 and instrument interface 404 in communication via bus 406. Bus 406, although shown as a single bus, may be implemented using multiple busses connected as necessary among the elements in the control processor 400.

The processor 402 and memory 410 provide the signal timing, processing and storage functions for the control processor 400. The I/O interface generally comprises the input and output mechanisms associated with the control processor 400. For example, the I/O interface 408 may comprise a keyboard, mouse, stylus, pointer, or other input mechanisms. The output portion of the I/O interface 408 may comprise a display, printer, or other output mechanism. The instrument interface 404 comprises the hardware and software used to couple the control processor 400 to the chromatograph 300 to enable communication and control between those elements. The power source 416 may comprise a direct current (DC) or an alternating current (AC) power source.

The memory 410 comprises instrument operating system software 414 and flow automation software 450. The instrument operating system software 414 comprises the instructions and executable code for controlling the operation of the chromatograph 300. In one example, the instrument operating system software 414 may be a proprietary operating system. The flow automation software 450 is a separate software module that can be integrated into the instrument operating system software 414 or can be implemented independently of the instrument operating system software 414. The flow automation software 450 can be invoked to allow a user of the chromatograph 300 to automatically and independently control multiple fluid pressures and fluid flows in the chromatograph 300. In an embodiment, the flow automation software 450 is programmed with the physical parameters (such as length and inner diameter of a chromatographic column) of the components in an analysis device and the parameters of the carrier gas to allow a user to maintain a desired flow in one or more fluid conduits by measuring and controlling the input and output pressures of the fluid conduits, and by measuring one or more temperatures and pressures within the chromatograph 300, as described above. Further, the flow automation software 450 allows accurate and repeatable analysis even of certain parameters of the physical plant of the chromatograph change over time or from analysis to analysis. For example, changing one of the columns of a chromatograph can change the fluid flow in the system. The physical parameters, e.g., the length and inner diameter, of the new column can be entered into the flow automation software 450 so that input and output pressures can be adjusted so that complex analyses can be duplicated, even if one or more components are changed.

In another embodiment of the system and method for controlling fluid flow, the flow automation software 450 can be used for what is referred to as method translation. Method translation refers to changing parameters of an analysis method. One example is doubling the speed of an analysis. By knowing all of the physical parameters of the components in the chromatograph, and by knowing the temperatures and the desired fluid flows, the flow automation software 450 can set the input and output pressures of the various fluid conduits so that the speed of analysis can be accurately doubled while maintaining relative retention of sample components.

In another embodiment of the system and method for controlling fluid flow, the flow automation software 450 can be used to adjust the input pressure of a chromatographic column so that the void time (the void time is the time it takes for a non-retained substance to traverse a column) is made the same as in a previous method to ensure that a peak elutes from the column at predictable retention times.

Figure 5:
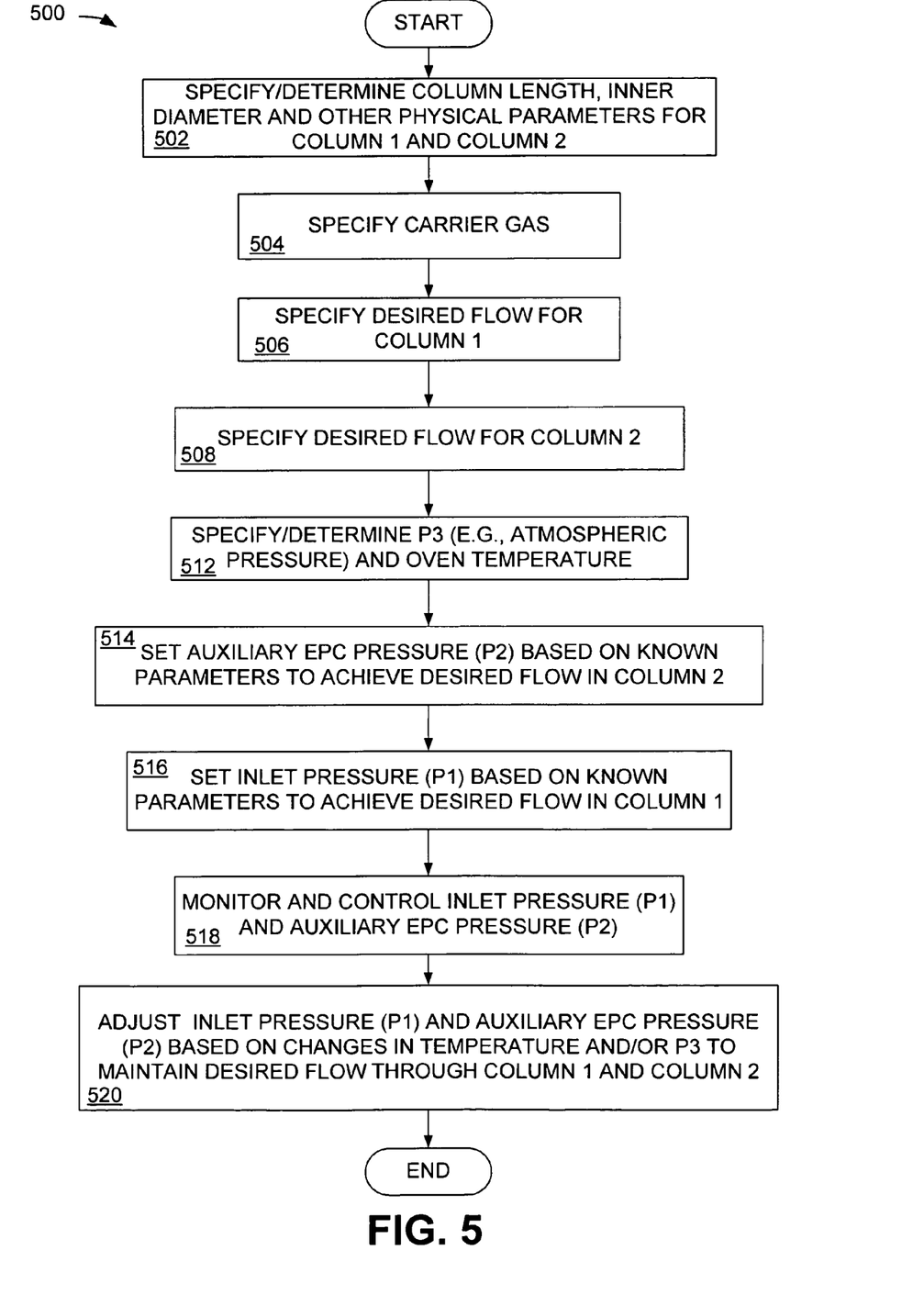
FIG. 5 is a flow chart illustrating the operation of an embodiment of the system and method for automating fluid flow as applied to a chromatographic analysis having two columns.

FIG. 5 is a flow chart illustrating the operation of an embodiment of the system and method for controlling fluid flow as applied to a chromatographic analysis having two columns. However, the principles of the system and method for controlling fluid flow apply to other fluid systems in which it is desirable to automate and control the flow of fluid through one or more fluid conduits. The blocks in the flowchart can be performed in the order shown or out of the order shown, or can be performed in parallel. In block 502, the length and inner diameter of each of the columns 310 and 312 is entered into the flow automation software 450. To calculate flow through open tubes, the "pneumatic resistance" of the column/tube must be known. This is easily accomplished if the column dimensions are known, as described above. In another embodiment, it is possible to deduce what is referred to as the "effective pneumatic resistance" of a column. For example, one way to determine the effective pneumatic resistance for a single column is to set known temperature and pressure conditions and determine the resulting retention time for a non-retained peak. By repeating this process using different sets of conditions, the column dimensions can be obtained mathematically. Alternatively, a "pneumatic resistance value", a mathematical function that substitutes for column dimensions in a flow calculation algorithm, can be used instead of the explicit column dimensions of length and diameter. As used herein, the term "entering" the length and diameter of each column, includes manually entering this information into the flow automation software 450, selecting the values from an available list, automatically inputting this information via a secondary reference to a column/tube identifier (e.g., tied to its part number, name, etc.), and empirically determining this information through manual or automated approach. In block 504, the physical parameters of the carrier gas are entered into the flow automation software. In an embodiment, the parameters of various carrier gasses may be included in a memory or library associated with the flow automation software 450 and entering the name of the carrier gas into the flow automation software 450 causes the flow automation software 450 to automatically obtain the carrier gas parameters from the memory. The terms determining and measuring may be used interchangeably.

In block 506, the desired flow of the first column 310 is entered into the flow automation software 450. In block 508, the desired flow of the second column 312 is entered into the flow automation software 450. The flow automation software 450 can apply rules and pre-determined constraints to limit the set of allowable values the user might input, so that total flow and flow through each section of tube are appropriate. For example, in a sealed serial combination of columns, the mass flow through each column section must be the same. So in this example, the flow automation software module could disallow entry of setpoints where the mass flow through the first column might theoretically exceed the flow through the second column.

In block 512, the control processor receives a signal representing the atmospheric pressure from the atmospheric pressure sensor 372, in this case representing the pressure P3, and receives a signal indicating the oven temperature from the temperature sensor 344. However, the pressure P3 may be obtained in other ways. The temperature sensor 344 measures the oven temperature. In block 514, the control processor 400 calculates appropriate pressure and causes the auxiliary EPC element 328 to set the pressure P2 to achieve the desired flow through the second column 312.

In block 516, the control processor 400 calculates the appropriate pressure P1 and causes the inlet EPC element 302 to set the pressure P1 to achieve the desired flow in the first column 310. In block 518, the control processor monitors and controls the inlet pressure P1 and the junction pressure P2. In block 520, the control processor 400 causes the inlet EPC 302 and the auxiliary EPC 328 to adjust the inlet pressure P1 and the junction pressure P2, respectively, based on desired flow changes as a function of time or in response to changes in temperature and atmospheric pressure. In this manner, independent control of the fluid flow through the first column 310 and the second column 312 is provided.

The system and method for controlling fluid flow is applicable to many embodiments in which not all coupled conduits are chromatographic columns. Examples where there are mixtures of conduits in series in which one or more of the conduits are not columns are provided below.

A "retention gap" is a column with no stationary phase that is typically used between an inlet and a column. Retention gaps impart desired features such as protecting a column from contaminants and allowing larger sample sizes to be injected—among other things. While the use of such conduits does not fall under the term "multidimensional chromatography," the fluid flow through such conduits can be controlled as described above. In addition, a retention gap may be implemented ahead of the first column in a multidimensional system wherein there is a second column following the first column. The system and method for controlling fluid flow could control such a system as a three-conduit system if the pressure at the junction between the retention gap and the first column were measured in addition to the pressure between the first column and the second column.

There are analysis applications in which one column is larger than another column. However, there is a downside in that the larger size column may create a problem when coupling to a mass spectrometer. For example, the column flow rate is too high for a mass spectrometer, or perhaps the inlet pressure is below atmospheric so air enters the system. By using a retention gap of smaller inner diameter, the inlet can operate at higher pressures and the chromatographic column actually operates under vacuum (which has some speed advantages). If these two conduits were coupled with a pressure monitored junction, the flow through the combined pair could be more accurately set.

In another example, effluent from the outlet of a column might be split to several detectors using appropriate restrictors. If a pressure controlled junction is used between the column and the restrictors, the flow in the column can be independently controlled. If all of the restrictor dimensions and outlet pressures are known, the flow through each restrictor, and the relative split ratio of flows into each path, can be calculated.

In another example, there are systems where none of the conduits are columns. An example is an application where it is desired to vaporize a sample and then direct the sample in a known fashion to multiple pathways (different analytical techniques each getting a portion). It is possible to use a conduit to connect the inlet to a purged splitter, and then have multiple restrictors leading to the multiple destinations. A flexible system would allow the split-path side to be operated somewhat independently from the flow from the initial introduction source.

In another example, assume that the flow from a first column is too large for a second column. A purged splitter could be implemented to which the second column and a restrictor are attached along with the first column. Effluent from the first column would travel into the splitter and then a portion of the effluent would travel to the second column, while the remainder of the effluent would travel to the restrictor to vent, or would travel to detector or another device. By knowing the dimensions of all paths and the inlet and outlet pressures of all paths, the flow to the second column could be set appropriately (independently from the flow from the first column) and the split ratio between the second column and the restrictor could be calculated.

The foregoing detailed description has been given for understanding exemplary implementations of the invention and no unnecessary limitations should be understood therefrom as modifications will be obvious to those skilled in the art without departing from the scope of the appended claims and their equivalents. Other devices may use the fluid coupling described herein.

What is claimed is:

1. A system for controlling fluid flow in a gas chromatograph, comprising:
   a first fluid conduit having a length, an inner diameter, an input pressure and an output pressure;
   a junction coupled to the first fluid conduit;
   a second fluid conduit coupled to the junction, the second fluid conduit having a length, an inner diameter, an input pressure and an output pressure, where a junction pressure comprises the output pressure of the first fluid conduit and the input pressure of the second fluid conduit;
   a pressure sensor coupled to the junction and configured to determine the junction pressure; and
   a controller coupled to the junction and the pressure sensor and configured to dynamically control the junction pressure by providing additional flow to the junction or by relieving excess flow from the junction in response to the junction pressure determined by the pressure sensor, thereby establishing and maintaining a desired fluid flow through the second fluid conduit independent of a flow through the first fluid conduit.

2. The system of claim 1, wherein the controller is further configured to set the flow through the first fluid conduit independently from the flow through the second fluid conduit.

3. The system of claim 2, wherein the first and second fluid conduits are chromatographic columns.

4. The system of claim 3, wherein at least one physical characteristic of the chromatographic columns is different.

5. The system of claim 2, wherein the controller continuously monitors an output pressure of the second fluid conduit, the temperature of the first fluid conduit and the temperature of the second fluid conduit, and alters the input pressure and the output pressure of the first fluid conduit to maintain a desired flow through at least one of the first fluid conduit and the second fluid conduit.

6. The system of claim 5, wherein maintaining a desired flow through the first fluid conduit can be performed independently from maintaining a desired flow through the second fluid conduit.

7. The system of claim 5 wherein a desired flow through the first fluid conduit can be established independent of the flow in the second fluid conduit based on at least one of the individual length and inner diameter of the first fluid conduit and the second fluid conduit.

8. The system of claim 5, wherein continuously controlling the output pressure of the first fluid conduit, and the temperature of the first fluid conduit and the second fluid conduit, allows multi-dimensional analysis to be performed.

9. The system of claim 5, wherein continuously monitoring the output pressure of the second fluid conduit, the temperature of the first fluid conduit and the temperature of the second fluid conduit, and entering the length and inner diameter of the first and second fluid conduits into the controller, and entering parameters of a carrier gas into the controller allows at least one component to be changed and an analysis to be accurately duplicated.

10. The system of claim 1, wherein more than two fluid conduits are coupled together.

11. A method for controlling fluid flow in a gas chromatograph, comprising:

entering a pneumatic resistance value of a first fluid conduit into a controller;

entering a pneumatic resistance value of a second fluid conduit into a controller;

entering physical parameters of a carrier gas into the controller;

entering a first desired fluid flow of the first fluid conduit into the controller;

entering a second desired fluid flow of the second fluid conduit into the controller;

adjusting an input pressure of the second fluid conduit based on an output pressure and temperature of the second fluid conduit, the length of the second fluid conduit, the inner diameter of the second fluid conduit, and physical parameters of the gas flowing through the second fluid conduit, wherein a junction pressure comprises the input pressure of the second fluid conduit and the output pressure of the first fluid conduit;

adjusting an input pressure of the first fluid conduit based on the junction pressure, the dimensions of the first fluid conduit, physical parameters of the gas flowing through first conduit, and the temperature of the first fluid conduit;

monitoring the input pressure and the output pressure of the first fluid conduit; and dynamically controlling the junction pressure by providing additional flow to the junction or by relieving excess flow from the junction, thereby establishing and maintaining a desired fluid flow through the second fluid conduit independent of a flow through the first fluid conduit.

12. The method of claim 11, wherein the first and second fluid conduits are chromatographic columns.

13. The method of claim 12, wherein at least one physical characteristic of the chromatographic columns are different.

14. The method of claim 11, further comprising:
continuously monitoring output pressure of the second fluid conduit, the temperature of the first fluid conduit and the temperature of the second fluid conduit; and altering the input pressure and the output pressure to maintain a desired flow through at least one of the first fluid conduit and the second fluid conduit.

15. The method of claim 14, wherein maintaining a desired flow through the first fluid conduit is performed independently from maintaining a desired flow through the second fluid conduit and the second fluid conduit allows predictable chromatography to be performed independently of the length and inner diameter of the first and second fluid conduits.

16. The method of claim 14, further comprising establishing a desired flow through the first fluid conduit independent of the flow in the second fluid conduit based on at least one of the individual length and inner diameter of the first fluid conduit and the second fluid conduit.

17. The method of claim 14, wherein continuously controlling the output pressure and the temperature of the first fluid conduit and the second fluid conduit, allows multi-dimensional analysis to be performed.

18. The method of claim 14, wherein continuously monitoring the output pressure of the second fluid conduit, the temperature of the first fluid conduit and the temperature of the second fluid conduit, and entering the length and inner diameter of the first and second fluid conduits into the controller, and entering parameters of a carrier gas allows at least one component to be changed and an analysis to be accurately duplicated.

* * * * *